US012285035B2

United States Patent
Del Bono et al.

(10) Patent No.: US 12,285,035 B2
(45) Date of Patent: Apr. 29, 2025

(54) COLONIC RELEASE FOOD SUPPLY AS A COADJUVANT IN THE TREATMENT AND PREVENTION OF COLONIC DISORDERS CAUSED BY A SUSPECTED OR CONFIRMED ALTERATION OF THE INFLAMMATORY PATTERN AND MICROBIOTA DESTABILIZATION

(71) Applicant: CRISTALFARMA S.R.L., Milan (IT)

(72) Inventors: Maria Cristina Del Bono, Milan (IT); Francesco Bonomo, Milan (IT)

(73) Assignee: CHRISTALFARMA S.R.L., Milan (IT)

( * ) Notice: Subject to any disclaimer, the term of this patent is extended or adjusted under 35 U.S.C. 154(b) by 715 days.

(21) Appl. No.: 17/616,209

(22) PCT Filed: Jun. 4, 2020

(86) PCT No.: PCT/IB2020/055271
§ 371 (c)(1),
(2) Date: Dec. 3, 2021

(87) PCT Pub. No.: WO2020/245760
PCT Pub. Date: Dec. 10, 2020

(65) Prior Publication Data
US 2022/0304354 A1 Sep. 29, 2022

(30) Foreign Application Priority Data

Jun. 6, 2019 (IT) ................. 102019000008265

(51) Int. Cl.
*A23L 29/262* (2016.01)
*A23L 33/105* (2016.01)
*A23L 33/12* (2016.01)
*A23L 33/135* (2016.01)
*A23P 10/20* (2016.01)
*A23P 10/30* (2016.01)
*A61K 9/20* (2006.01)
*A61K 36/324* (2006.01)
*A61K 36/61* (2006.01)

(52) U.S. Cl.
CPC ........... *A23L 29/262* (2016.08); *A23L 33/105* (2016.08); *A23L 33/12* (2016.08); *A23L 33/135* (2016.08); *A23P 10/20* (2016.08); *A23P 10/30* (2016.08); *A61K 9/2054* (2013.01); *A61K 36/324* (2013.01); *A61K 36/61* (2013.01)

(58) Field of Classification Search
None
See application file for complete search history.

(56) References Cited

FOREIGN PATENT DOCUMENTS

| EP | 3409275 A1 | * 12/2018 | ............. A61K 36/67 |
| WO | 2015087259 A1 | 6/2015 | |

OTHER PUBLICATIONS

Cristalfarma, internet article, https://web.archive.org/web/20170811181004/https://www.cristalfarma.it/it/prodotti/ibidi.html, 2017. (Year: 2017).*
Geirnaert, Sci Rep 7, 11450 (2017). (Year: 2017).*
Anonymous: "Ibridi—cristalfarma", 2014, pp. 1-2.
Anonymous: "Sodium alginate", in "Handbook of Pharmaceutical Excipients, 6th ed.", 2009, Pharmaceutical Press, pp. 622-624.
Modasiya M.K. et al., "Design of colon specific drug delivery using sodium alginate and HPMC", Journal of Pharmacy Research, vol. 5, No. 4, Apr. 2012, pp. 2253-2258.
Petti L. et al., "In vitro anti-inflammatory and protective effects of ibidi on intestinal epithelial cells", European Journal of Medicinal Plants, vol. 4, No. 9, 2014, pp. 1022-1035.
Rogerls T. L., "Hypromellose", in "Handbook of Pharmaceutical Excipients", Feb. 20, 2009, Pharmaceutical Press, pp. 326-329.
Search Report and Written Opinion of PCT/IB2020/055271 of Sep. 10, 2020.
Torres J. et al., "European Crohn's and colitis organization topical review on complementary medicine and psychotherapy in inflammatory bowel disease", Journal of Chron's and Colitis, vol. 13, No. 6, Mar. 2019, pp. 673e-685e.

* cited by examiner

*Primary Examiner* — Layla D Berry
(74) *Attorney, Agent, or Firm* — Silvia Salvadori, P.C.; Silvia Salvadori

(57) ABSTRACT

Oral tablet comprising as active principle an association of dry extracts of turmeric, pomegranate and *Boswellia*, with colonic release, wherein said release is guaranteed by the presence of a combination of sodium alginate and hydroxypropyl methylcellulose in the relative matrix in which the aforementioned active ingredients are dispersed. This oral tablet, preferably in the form of a food supplement, is employed as co-adjuvant in the treatment and prevention of colonic disorders caused by suspected or confirmed alteration of the inflammatory situation and destabilization of the microbiota.

13 Claims, 7 Drawing Sheets

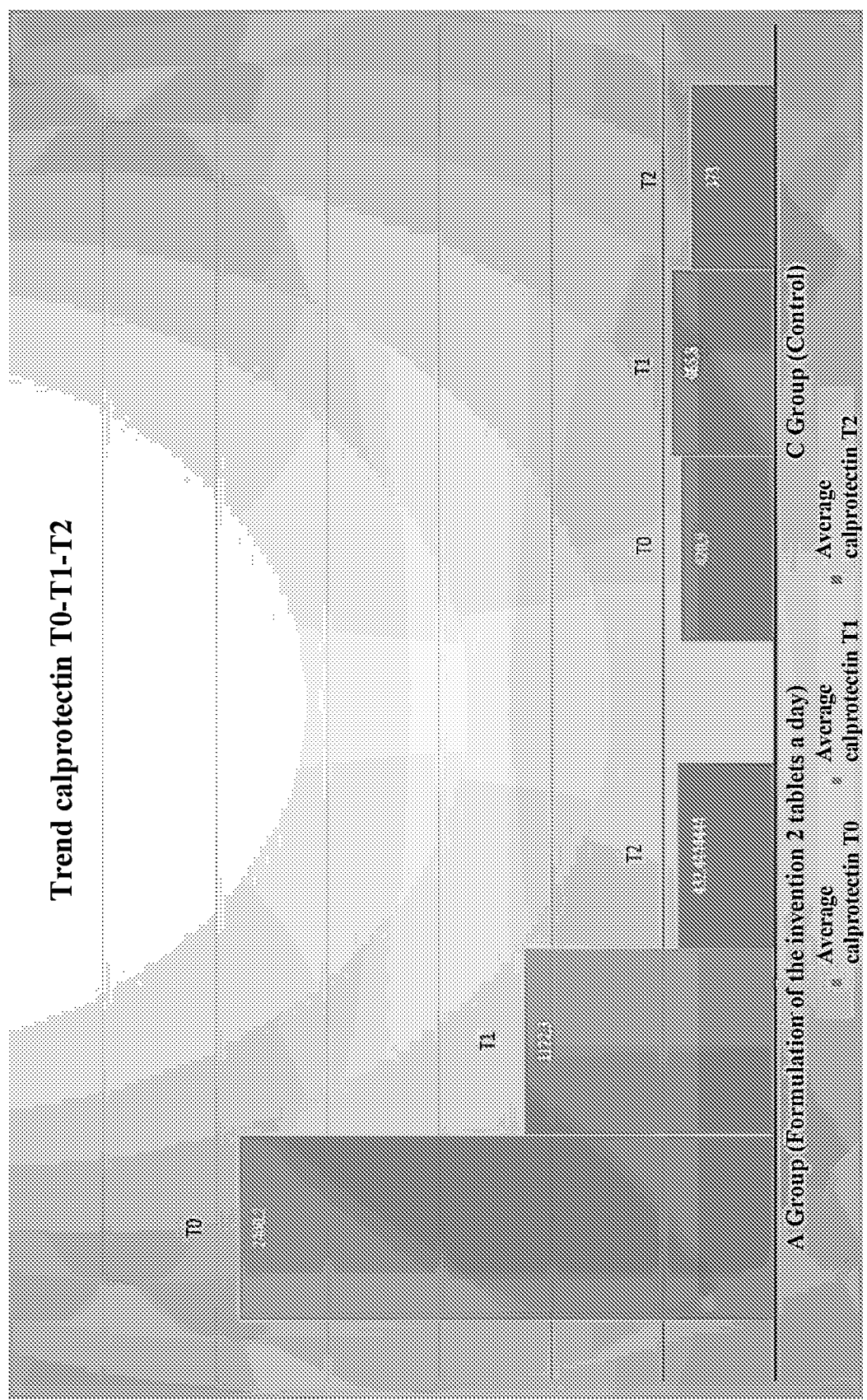
Fig 4/A

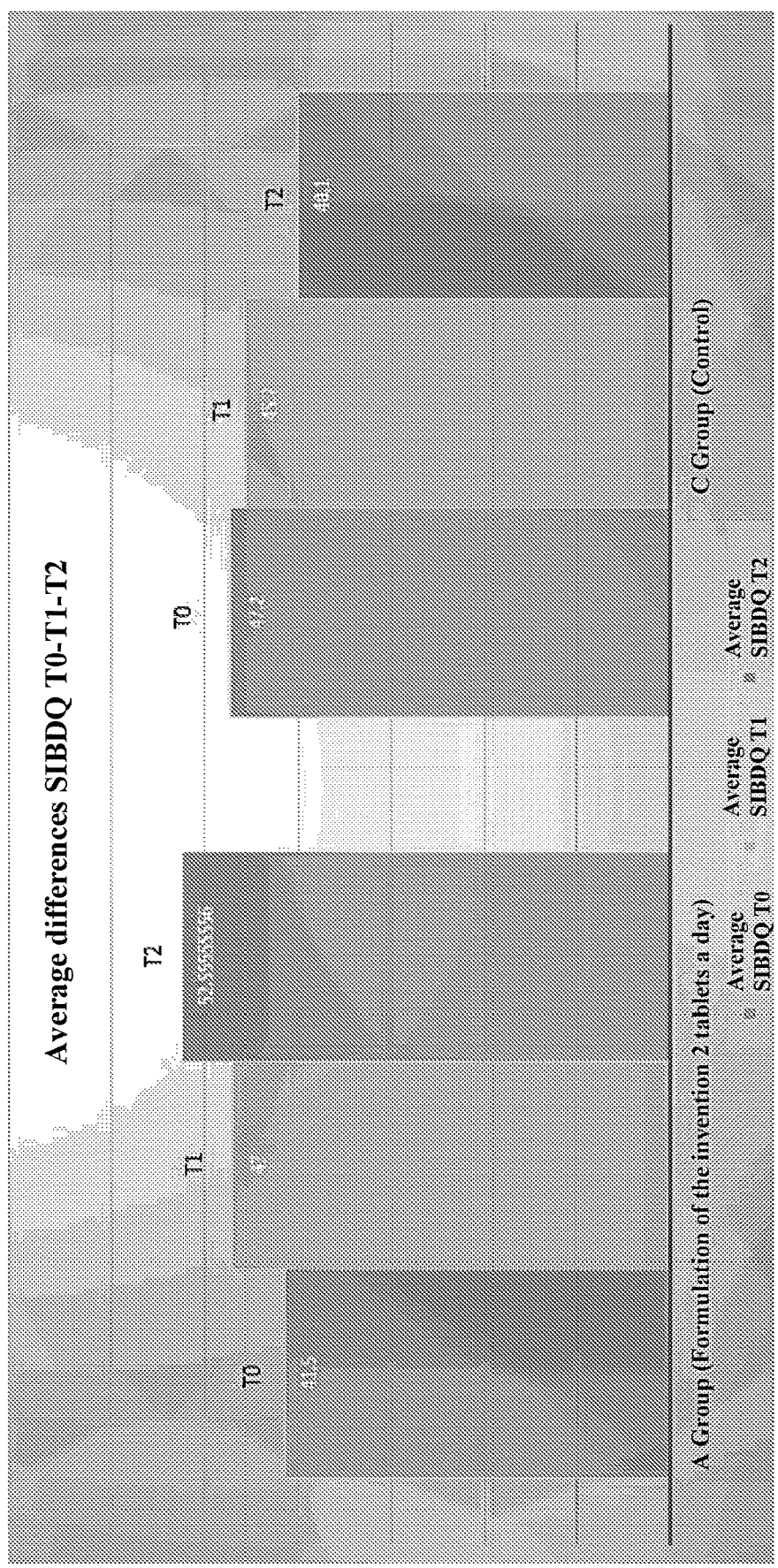
Fig 4/B

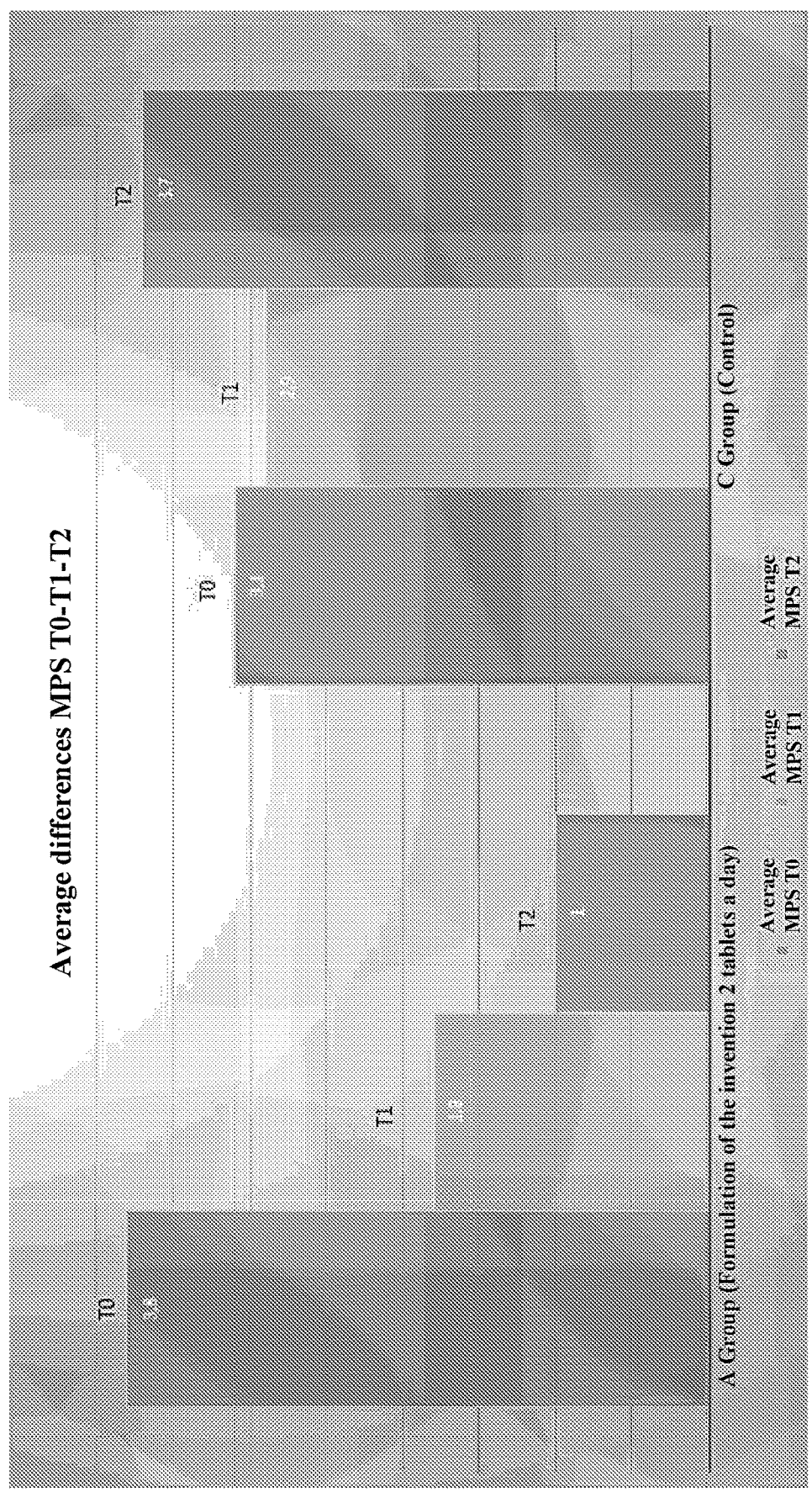
Fig 4/C

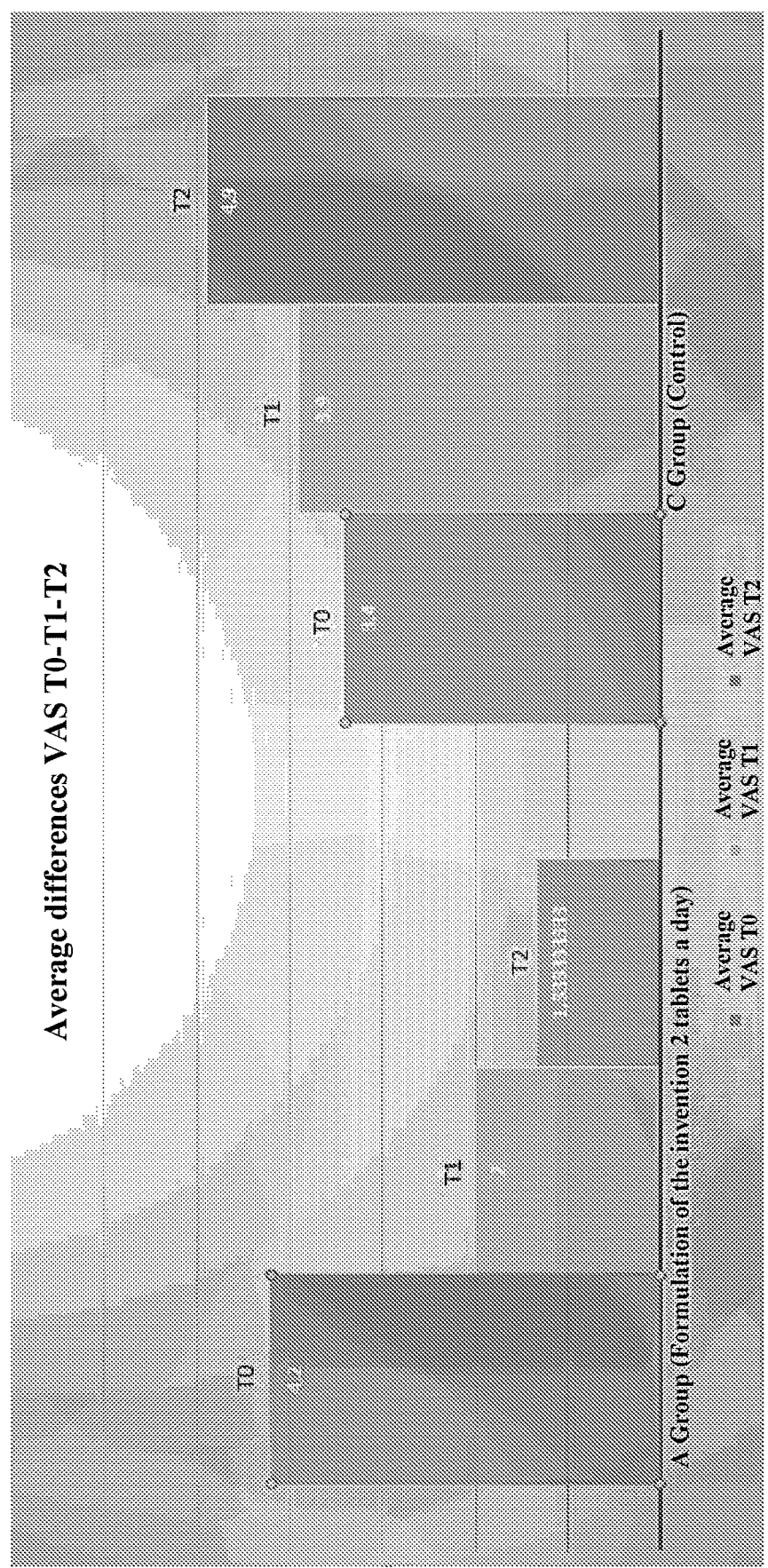
Fig 4/D

COLONIC RELEASE FOOD SUPPLY AS A COADJUVANT IN THE TREATMENT AND PREVENTION OF COLONIC DISORDERS CAUSED BY A SUSPECTED OR CONFIRMED ALTERATION OF THE INFLAMMATORY PATTERN AND MICROBIOTA DESTABILIZATION This application is a U.S. national stage of PCT/IB2020/055271 filed 4 Jun. 2020, which claims priority to and the benefit of Italian Application No. 102019000008265 filed on 6 Jun. 2019, the contents of which are incorporated herein by reference in their entireties.

FIELD OF THE INVENTION

The present invention relates to an oral tablet, in particular in the form of a colonic release food supplement, as a co-adjuvant in the treatment and prevention of colonic disorders caused by suspected or confirmed alteration of the inflammatory pattern and microbiota destabilization.

STATE OF THE ART

According to what reported by Treccani encyclopaedia inflammation in medicine is the complex of reactive events involving the tissues of higher animal bodies when they come into contact with harmful agents of different nature[1]. The most frequent result of this process is neutralization of the harmful agent or confinement of the lesion produced therefrom. The causes of inflammation may be of physical, chemical and biological nature, even if some inflammatory diseases are still being studied as concerns identification of specific aetiological agents. The inflammatory reaction is determined by vascular and cellular events. The inflammation clinical events have been known since the classical antiquity: calor, rubor, tumor, dolor and functio laesa. They correspond, in this order, to the apparent events related to inflammation: blood vessels appear dilated, with an increase in the local circulation (hyperaemia: rubor, calor); plasma (plasmatic exudation), some formed elements of the blood (diapedesis) represented by granulocytes, lymphocytes, plasma cells, and, exceptionally, red blood cells, outflow therefrom, which are added by cell elements coming directly from the tissues (hystogenic reaction) with resulting swelling (tumor) of the inflamed part1. The latter is also deeply aching (dolor) and functionally impaired (functio laesa). Based on the extent of the vascular and cellular responses to inflammatory stimuli it is possible to distinguish two main types of inflammations: the acute ones, wherein vascular events prevail on cellular events (exudation phlogosis), and the chronic ones, wherein cellular events prevail on vascular events (productive phlogosis). Inflammation can occur in any human body tissue and consequently affect all organs and apparatuses. When the inflammatory process affects the bowel mucous membrane we can observe an extremely variable range of clinical diseases, which can result also in mild forms with few symptoms. Among the diseases where the confirmed or suspected inflammation/hyperimmunity is the focus of the disease and of disorders suffered from the patients, we can include, for exemplary and non-limiting purposes, various different forms of colitis (indeterminate, collagen, from drugs, non-specific . . . ), some sub-classes of diverticular disease (symptomatic uncomplicated diverticulosis disease SUDD, diverticulitis, segmental colitis associated with diverticulosis SCAD, irritable colon syndrome IBS . . . ) up to more severe and debilitating inflammatory bowel diseases IBD (Ulcerative rectocolitis RCU, Chron's disease). An aetiologic factor which is thought to have a key role in the pathogenesis of the intestinal inflammation and which is worth focusing the attention is the intestinal microbiota[2]. To better explain this it must be noted that microbiota is considered by the scientific community as a real «protective organ» of the gastrointestinal system.[2] In this respect it is often noted that, among other functions, it is able to regulate the bowel local immune system consequently controlling all the inflammatory processes that can affect the mucous membrane. The mechanisms implemented by the intestinal microbiota to guarantee the correct functioning of the intestinal immune system are variable and involve adjusting more factors[2]. When the intestinal microbiota loses its functional integrity an abnormal activation of the adaptive immune system takes place, the one which involves some lymphocyte species of the T helper line (Th1, Th2, Th17), NF-kB factor deregulation, higher leukocyte activity and increase in the oxidative damage3-5. The activation of Th1 and Th17 lines leads to an increase of IL-1, IL-6, IL-8 IL-2, IL-17, TNF alpha and IFN-y, that are known pro-inflammatory cytokines which, in addition to activating and supporting phlogosis, interact with macrophages and APC (a cell containing the antigen) amplifying the activity thereof and cytokine production[3-5]. The activation of the Th2 line determines the increase of cytokines IL-5, IL-13 where IL-5 is also the signal which activates the Natural Killers[3-5]. The infiltration of leukocytes into the intestine, if no longer under control, supports and amplifies phlogosis of the mucous membrane. Leukocytes are in fact attracted by cytokines and chemokines produced by various blood white cells, and once arrived at the inflamed tissue, they increase the structural damage[5,6]. An inflammatory marker that is commonly measured to determine an intestinal inflammation is faecal calprotectin. Calprotectin is a protein belonging to the S100 family and is contained in great amounts in neutrophil granulocytes, where it accounts for 5% of the total proteins and for 60% of cytoplasmic proteins. Calprotectin has been found, in lower amounts, also in activated monocytes and macrophages. In presence of inflammatory processes, calprotectin is released after granulation of neutrophil granulocytes. In case of a bowel inflammation, calprotectin can be detected in faeces. Other observed haematochemical parameters, though less faecal calprotectin-specific, are ESR and CRP. In pharmacological terms, literature review highlights that many molecules used to treat bowel chronic inflammations are associated to controlled-release technologies with the objective to optimize its efficiency reducing at the same time the possible typical side effects of these drugs. In 2015 the World Journal of Gastrointestinal Pharmacology and Therapeutics (Bei Ye et al. Mesalazine preparations for the treatment of ulcerative colitis: Are all created equal? World J Gastrointest Pharmacol Ther. 2015 Nov. 6; 6(4): 137-144.) published a review evaluating the difference between the different mesalazine-based formulations existing in the literature, stressing the fact that all the formulations analysed are provided with modified-release technologies; this explains the scientific interest towards such types of release. The following table reports formulations examined by the review.

| Formulations | Generic name | Proprietary names | Mode of delivery | Site of drug release |
|---|---|---|---|---|
| Azo-bonded prodrugs | Sulfasalazine | Azulfidine ®, Salazopyrin ®, Pyralin ® | Mesalazine bound to sulfapyridine | Colon |
| | Olsalazine | Dipentum ® | Two mesalazine molecules bound together | Colon |
| | Balsalazide | Colazide ®, Colazal ® | Mesalazine bound to 4-aminobenzoyl-β-alamine | Colon |
| pH dependent | Mesalazine | Asacol ®, Mesren ® | Eudragit-S coating (dissolves at pH ≥ 6) | Terminal ileum, colon |
| | | Salofalk ®, Mesasal ®, Claversal ® | Eudragit-L coating (dissolves at pH ≥ 7) | Mid ileum to colon |
| | | Salofalk Granules ® | Eudragit-L coating and matrix core | Mid ileum to colon |
| Time dependent | Mesalazine | Pentasa ®, Pentasa ® granules | Microspheres encapsulated within an ethycellulose semi-permeable membrane | Duodenum to colon |
| MMX | MMX mesalazine | Lialda ®, Mezavant XL ®, Mezavant ® | Enteric coating (dissolves at pH ≥ 7), MMX of liphilic and hydrophilic excipients | Terminal ileum and entire colon |

This type of essentially pharmacological therapies has serious drawbacks related to the use of drugs such as for example steroidal drugs which have a considerable range of undesired side effects.

Besides pharmacological therapies, of which the above mentioned ones are only some proposed by traditional medicine, CAM therapies (Complementary and Alternative Medicine) are being increasingly studied as a support to the treatment of inflammatory-based diseases, even when the concerned organ is the bowel. In this regard there is some literature evidence reporting the scientific interest on colonic release technologies even when applied to botanicals (plant extracts), the Journal of Pharmacy Research in 2012 (M. K. Modasiya et al./Journal of Pharmacy Research 2012, 5(4), 2253-2258) published data on some specific technologies applied to curcumin. There exists on the market an oral formulation with the trade name of IBIDI® as a disease co-adjuvant in the treatment of colonic disorders caused by a suspected or confirmed alteration of the inflammatory pattern and microbiota destabilization comprising as active ingredients at least 3 botanicals (*Boswellia*, Turmeric and *Punica granatum*), dispersed in a hydroxypropyl methylcellulose-based matrix.

In fact curcumin is the active ingredient contained in *Curcuma longa*. Curcumin regulates the inflammatory processes inhibiting the expression of several cytokines as IFN-γ, TNF alpha, IL-1beta and IL-12. Curcumin itself has revealed efficient in inhibiting activation of the NF-kB factor, in activating PPAR-γ genes, in inhibiting the release of COX2 and finally in reducing the NO levels that are notoriously high in patients affected with IBD[7-11]. In a study carried out in 2013 the synergistic effect between curcumin and antibiotics and the antibacterial effect of curcumin against *S. aureus*-resistant strains were investigated. Besides a significant activity exhibited by turmeric with respect to 10 *S-aureus*-resistant strains, turmeric guaranteed a reduction of antibiotic MICs with respect to oxacillin (OXI), ampicillin (AMP), ciprofloxacin (CIP), and norfloxacin (NOR), confirming the synergistic effect[12,13]

*Boswellia serrata*: *Boswellia* regulates the cytokine release, inhibits the NF-kB factor activation and, mainly due to its boswellic acid AKBA, reduces the leukocyte activity interfering on the rolling and the endothelium cell adhesion[14,15] In an in vitro study the antimicrobial capacities of the boswellic acids (AKBA, KBA, BA) on 112 bacterial species were analysed. The pathogenic species commonly present inside the gastro-intestinal tract were taken into consideration: *E. fecalis, E. faecium, S. aureus*, etc. . . . . . MICs obtained for these species have demonstrated that the boswellic acid that is mostly active in terms of antimicrobial action is the 11-keto-beta-boswellic acid (AKBA): *E. faecalis*→average MIC 6 µg/ml; *E. faecium*→average MIC 6 µs/ml; *S. aureus*→average MIC 2 µg/ml[16].

Pomegranate promotes the selective growth of bowel bacteria supporting the microbiota. Together with the prebiotic action, the pomegranate extract leads the microbiota to produce SCFAs (short chain fatty acids) among which the beneficial butyric acid and to promote urolithin release, known endogenous anti-inflammatories[17].

Even if this type of formulation represents a good therapy supporting conventional treatments, which only provide for drug treatments, it has a number of drawbacks in that some of the active ingredients are hardly soluble and/or are almost completely degraded in the stomach, and furthermore it is not sure whether they are released in sufficient amounts in the colon where inflammatory processes are taking place.

"Handbook of Pharmaceutical Excipients", 6$^{th}$ ed., 2009, Pharmaceutical Press, XP055514625, pages 622-624 describes the properties of alginate and reports that it can be used in a matrix to slow down active ingredient release.

"Handbook of Pharmaceutical Excipients", 20 Feb. 2009 (2009 Feb. 20), Pharmaceutical Press, XP055325597, ISBN: 978-0-85369-792-3 pages 326-329, describes similar controlled release properties for hydroxypropyl methylcellulose.

WO 2015/087259 A1 discloses tablets containing curcumin dispersed into a matrix consisting of hydroxypropyl methylcellulose, tablets that must always be coated with a gastro-resistant film to be effective for treating bowel inflammatory diseases.

JOANA TORRES ET AL: "European Crohn's and Colitis Organisation Topical Review on Complementary Medicine and Psychotherapy in Inflammatory Bowel Disease", JOURNAL OF CROHN'S AND COLITIS, vol. 13, no. 6, March 2019 (2019-03), pages 673-685, shows the use of several plant extracts for treating bowel inflammatory diseases. In Table 1 a multitude of plant extracts among which turmeric, *Boswellia* and pomegranate is listed.

SUMMARY OF THE INVENTION

The Applicant has found out that it is now possible to overcome the problems of the tablet of the background art by the tablets object of the present invention, which are more gastro-resistant than the commercially available IBIDI® formulations, as will be better disclosed hereinafter.

The object of the present invention is therefore a colonic release oral tablet comprising as active principle a mixture of dry extracts of turmeric, pomegranate and *Boswellia*, wherein said release is guaranteed by the presence of a combination of sodium alginate and hydroxypropyl methylcellulose in the relative matrix in which the aforementioned active ingredients are dispersed.

This tablet is in particular used as a co-adjuvant in the treatment and prevention of colonic disorders caused by a suspected or confirmed alteration of the inflammatory pattern and destabilization of the microbiota.

The Applicant has in fact unexpectedly found that sodium alginate and hydroxypropyl methylcellulose act in synergy guaranteeing uniform release rheological profiles, that can be reproduced and independent from the hydrophilic, lipophilic or amphiphilic nature of the carried active ingredient.

Figure 1:
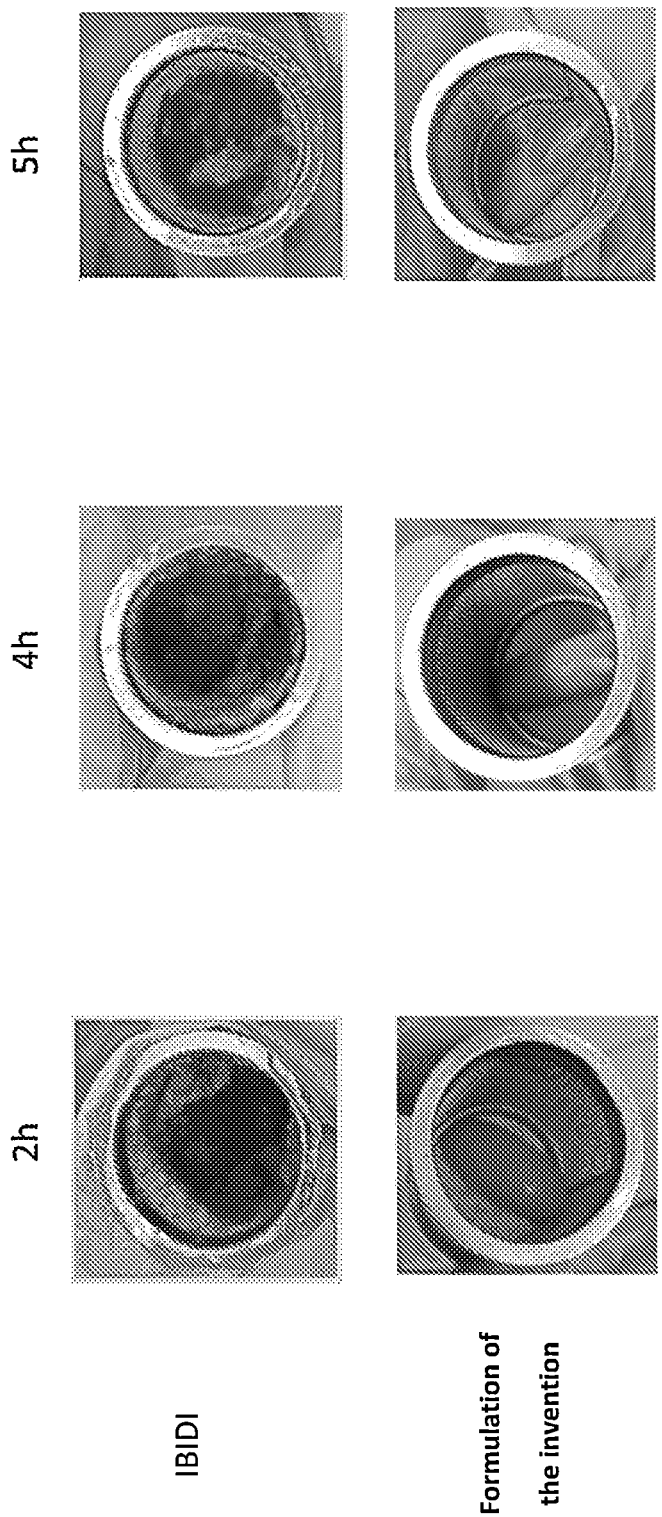
FIG. 1 reports the results of the test disclosed in the example 2, after 2, 4 and 5 hours of breakdown carried out respectively on the IBIDI® tablet and on the formulation of the invention, in particular the tablet whose composition is reported in the example 1.

The FIGS. 4-A, 4-B, 4-C, 4D report the results of the clinical trial disclosed in the Example 4, at time T1=3 months and at time T2=6 months, carried on a group (A) of patients suffering from RCU, who, in addition to the conventional therapy were administered two tablets a day according to the present invention and compared with a group of patients (C), suffering from the same disease who were only administered the conventional therapy.

DETAILED DESCRIPTION OF THE INVENTION

Preferably the sodium alginate and hydroxypropyl methylcellulose are present in ratios comprised between 1:25 and 1:10, more preferably between 1:20 and 1:15. According to a particularly preferred embodiment said ratio is 1:19.

Preferably to promote the colonic release the tablets object of the invention also contain dry extract of black pepper. In fact, black pepper coming from the fruits of the *Piper nigrum* L plant promote the enteric uptake of substances that are not easily soluble, such as for example boswellic acids (http://www.cosmofarma.com/wpcontent/uploads/2017/06/www.cosmofarma.com/Fratter_2.pdf).

In order to guarantee the increase of the contact surface between the active substance and the inflamed intestinal epithelium, the product was formulated with excipients which ensure the colonic release of the functional components protecting integrity thereof while passing through the gastric environment and into the first intestinal tract. In order to comply with such requirements the tablet preferably provides for a gastro-resistant coating ensured by the presence of shellac in the film. As underlined in the summary of the invention, the integrity of the tablet, while crossing the first intestinal tract, is promoted by the presence, in the core, of sodium alginate and hydroxypropyl methylcellulose which ease the release of the majority of the active components in the distal portion of the bowel by prolonging breakdown times. Once released in the enteric secretions, they will result into a prompt dissolution and hydro-dispersion of active ingredient (boswellic acid salification) \ and (hydro-dispersion of the curcuminoid fraction as a response to the alkaline environment).

Preferably in the oral tablet object of the present invention the dry extract of turmeric comes from the *Curcuma longa* L rhizome, and has a minimum titre in curcumin and curcuminoids of 90% preferably of 95%.

According to another preferred embodiment the dry extract of pomegranate comes from the fruit of *Punica granatum* L. and has a minimum titre in ellagic acid of 20%, preferably of 40%.

According to a further preferred embodiment the dry extract of *Boswellia* comes from the *Boswellia serrata* Roxb. gum resin and has a minimum titre in boswellic acids of 30% preferably of 65%.

Finally, according to a further preferred embodiment the black pepper extract possibly present comes from the fruits of the *Piper nigrum* L. plant with a minimum titre in piperine of 80% preferably of 95%.

Preferably the oral tablet object of the invention wherein the turmeric is contained in amounts comprised between 80 and 150 mg by weight on the total weight of the tablet, more preferably in amounts equal to 100 mg, the *Boswellia* is contained in amounts comprised between 150 and 300 mg, more preferably 200 mg, the dry pomegranate extract is contained in amounts between 200 and 350 mg, more preferably 250 mg by weight on the total weight of the tablet.

As noted above, when the oral tablet contains black pepper, it is preferably contained in an amount comprised between 1 and 5 mg, more preferably 2 mg by weight on the total weight of the tablet.

The tablet object of the invention can possibly also contain probiotics such as for example *Lactobacillus plantarum, Lactobacillus paracasei* and/or post-biotics among which short chain fatty acids (SCFA) and other active metabolites of the intestinal microbiota.

Preferably said colonic disorders caused by suspected or confirmed alteration of the inflammatory pattern and destabilization of the microbiota are preferably selected from colitis selected from indeterminate, collagen, from drugs and non-specific, diverticular diseases selected among symptomatic uncomplicated diverticulosis or SUDD, diverticulitis, segmental colitis associated with diverticulosis SCAD, inflammatory bowel diseases selected from Ulcerative rectocolitis RCU, Chron's disease, IBS (Irritable Bowel Syndrome)

Preferably the tablet according to the present invention is included in the category of food supplements and according to a particularly preferred solution it is administered twice a day.

In addition to the aforesaid components, the tablets object of the present invention can also contain conventional excipients used in the pharmaceutical art which are well known to the expert in the field.

The following examples of compositions of the tablet object of the present invention, as well as laboratory tests and clinical trials are hereinafter reported, for exemplary and non-limiting purposes.

Example 1

The following example of a specific formulation of the tablet object of the invention is hereinafter reported.

| Active COMPONENTS | DOSES per TABLET |
|---|---|
| Curcuma longa dry extract rhizome min. 95% | 100 mg |
| Of which curcumin | 95 mg |
| Boswellia serrata dry extract | 200 mg |
| From which boswellic acids | 130 mg |
| Punica granatum dry extract | 250 mg |
| From which ellagic acid | 100 mg |
| Black pepper dry extract, | 2 mg |
| From which piperine | 1.9 mg |
| Excipients per tablet | |
| hydroxypropyl Methylcellulose-E464 | 190 mg |
| Calcium phosphates E341(ii) | 175 mg |
| Cellulose-E460(i) | 169 mg |
| Magnesium salts of fatty acids-E470b | 11 mg |
| Sodium alginate E401 | 10 mg |
| Silicon dioxide E551 | 5 mg |
| Shellac-E904 | 33 mg |
| Glycerol-E422 | 4.1 mg |
| Fatty acids-E570 | 2.4 mg |
| Titanium dioxide-E171 | 2 mg |
| Iron oxides and hydroxides-E172 | 0.9 mg |

Example 2—Comparative Evaluation Between Ibidi Tablet without Coating and the Tablet with the Formulation Reported in the Example 1, without Coating An approach is proposed evaluating the performance of the tablet according to the invention and the IBIDI tablet in two tests used as reference by Pharmacopoeia.

The evaluation proposed determines the formulation resistance according to the present invention to the gastric environment (breakdown test) and the release time in an intestinal environment of one of the components, the pomegranate ellagic acid. The dissolution time will be the parameter which will allow to estimate the powder release site based on the bowel transit time.

Breakdown Test

The sample will be tested in the breakdown assay, using equipment and operating conditions as described in Pharmacopoeia. In particular, reference will be made to the conditions and limits provided for validating gastro-resistant tablets (medium: HCl 0.1 N, for two hours with no clear alteration; subsequent breakdown in phosphate buffer at pH 6.8 within 60 minutes at a temperature of 36-38° C.).

Dissolution Test

The sample was tested in the dissolution assay, using equipment and operating conditions as described in Pharmacopoeia, using an instrument with cylindrical containers, provide with hemispheric bottom with a blade or basket stirrer Dissolution Medium:

Starting by an "acid cycle": 750 ml HCl 0.1M for 2 hours. Subsequent "buffer cycle" to add 250 ml of $Na_3PO_4$ 0.2M for 45-60 minutes Alternatively it may be used:

"Acid cycle": 1000 ml HCl 0.1M for 2 hours. Removal of the acid initiation of the "Buffer cycle": 1000 ml buffer solution pH 6.8 for 45-60 minutes.

The results carried out with the breakdown test are reported in FIG. 1. The photos highlight the gastro-resistance efficacy of the tablet according to the present invention as after 5 hours from insertion into acid liquid the tablet remains intact; the formula without HPMR technology is dissolved already after the first 2 hours in an acid environment.

Figure 2:
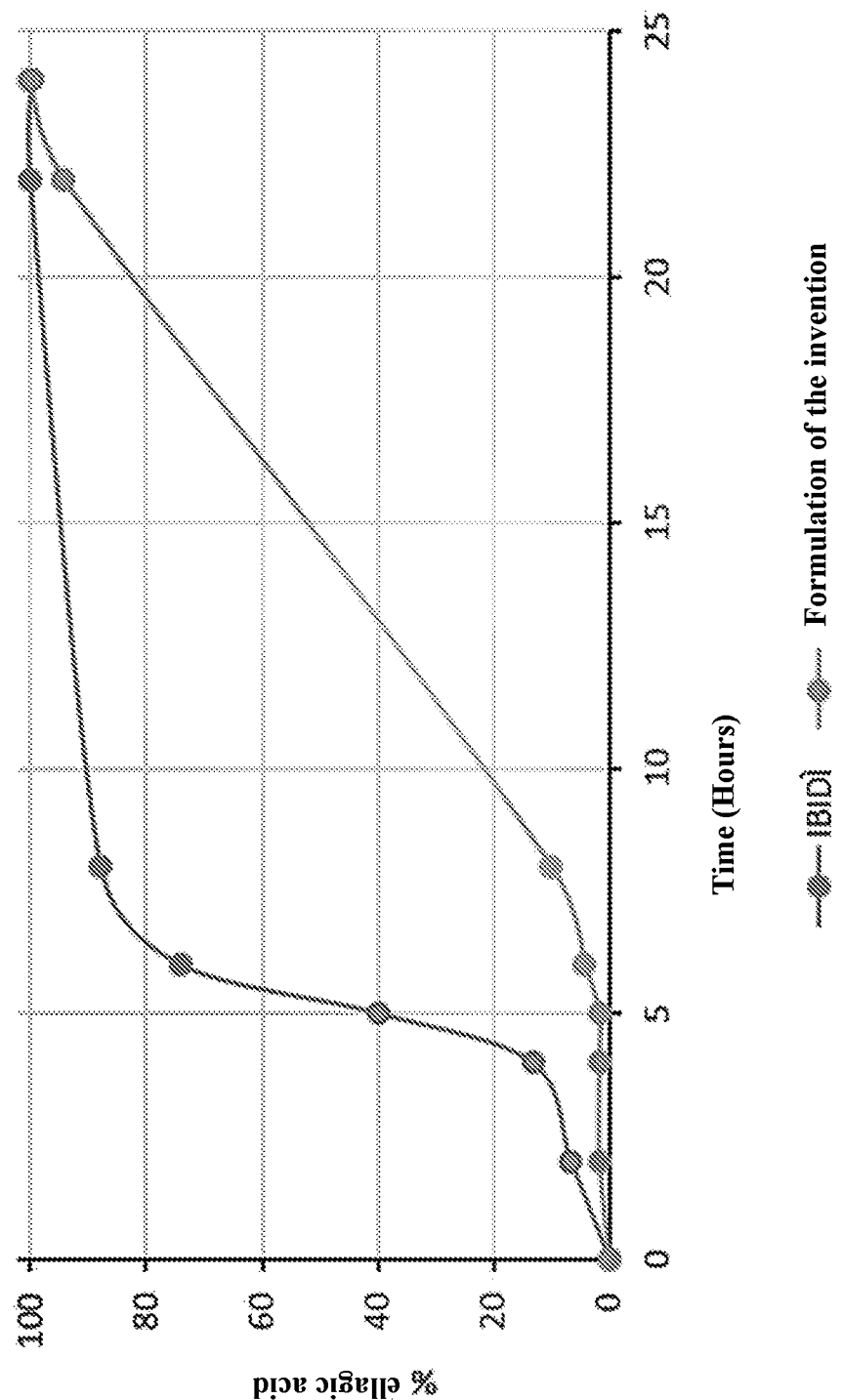
FIG. 2 instead reports the dissolution test disclosed in the Example 2 of the ellagic acid that is the main component contained in the pomegranate and in turn contained in the formulation according to the present invention, where the diagram on the left reports the dissolution test of known IBD formulations while the diagram on the right reports the release of the formulations of the invention.
Figure 3:
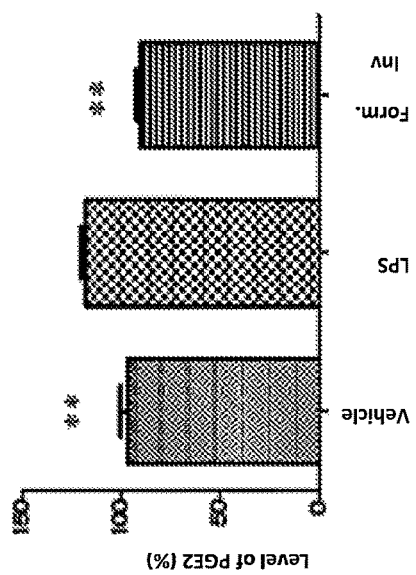
FIG. 3 reports the results of the ex vivo test, disclosed in the Example 3, carried out on a pattern of intestinal cells simulating IBD, on the effectiveness of the tablet according to the invention, in particular the tablet whose composition is reported in the Example 1.
Figure 3:
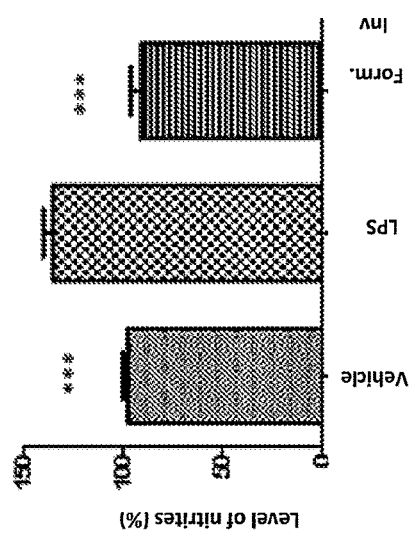
Figure 3:
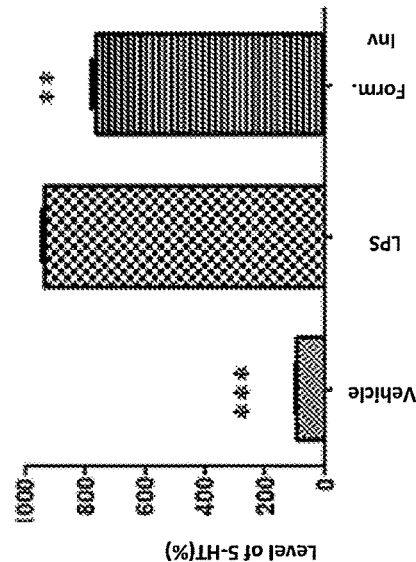

The results of the dissolution tests reported in FIG. 2 carried out only on the ellagic acid contained in both the tablets (IBIDI and the tablet of the example 1) highlights that the release of the aforesaid active ingredient from the tablet according to the present invention is compatible with the slow release concept, thus compatible with a colonic release, if compared to the much faster release profile of the ellagic acid contained in the known IBIDI tablet.

Example 3 Effectiveness Evaluation in an Ex Vivo Experimental Model of IBD (Inflammatory Bowel Disease) Mouse The sample was tested on an ex vivo experimental model of mouse. The effect of the presence of graded concentrations of the tablet of the invention in the culture medium was evaluated quantitatively determining specific markers of oxidative stress and inflammation attributable to morphological and structural alterations of a chronic inflammation of the colon mucous membrane.

The parameters taken into consideration are the following: effects on the nitric oxide synthase and quantification of the thiobarbituric acid derivatives as stable markers of lipid peroxidation, the effect on the activity of pro-inflammatory cytokines as prostaglandin E2 and serotonin.

The results of such test are reported in FIG. 2.

From these results it derives that the tablet object of the invention is able to:

determine a significant reduction of nitrite levels, nitrosative stress indexes due to increased production in nitric oxide by the inducible isoform of the nitric oxide synthase (iNOS) in the bowel;

reduce 5-HT levels in the colon of LPS-stimulated mouse (inflammatory stimulus);

reduce tissue levels of serotonin and PGE2, which play a key role as pro-inflammatory cytokines in ulcerative colitis.

Example 4—Clinical Trial

A clinical trial was designed to verify the effectiveness of the tablets of the invention, versus control, in optimizing the recrudescence therapy in a mild-moderate activity step of ulcerative rectocolitis by monitoring the quality of life (by means of the sibdq), phlogosis indexes among which the Faecal Calprotectin, clinical activity indexes (mayo partial score) and perceived abdominal pain (VAS scale).

PROTOCOL: 20 patients suffering from active RCU (diagnosed with standard criteria) in need of a therapy for treating recrudescence were recruited:

10 patients received the recrudescence therapy (deltacortene, budesonide MMX and/or rectally)—GROUP C (control)

10 patients received the tablets object of the invention, whose composition is reported in the Example 1, in addition to the recrudescence therapy (deltacortene, budesonide MMX and/or rectally)—GROUP A Duration of the study: 6-month treatment with follow-up after 3 months.

Posology: The patient arm being treated with the tablets object of the invention will take 2 tablets a day in addition to the commonly prescribed therapy.

The clinical lab evaluation (at T0, T1 e T2) will envisage:
Evaluation of inflammatory parameters; for example faecal calprotectin.
Evaluation of the Mayo Partial Score (MPS) for clinical activity
Evaluation of the abdominal pain VAS scale
Evaluation of the faeces consistency Bristol Stool Chart
Submitting the SIBDQ questionnaire for evaluating the quality of life.

Inclusion Criteria:
Age 18-75 years old
Clinically-ascertained RCU diagnosis in a mild-moderate activity step (MPS between 2 and 7), in need of a steroid therapy for treating recrudescence.

Exclusion Criteria
RCU of the only rectum (E1)
Patients previous submitted to colectomy
Patients being treated with an immuno-suppressant or biologic drug or in need of drugs for recrudescence.
Patients scoring MPS<2 or >7.

Operative Sheet
T0 recruitment
Clinical evaluation of the disease status with Mayo Partial Score, Bristol Stool Chart, pain VAS scale, inflammatory indexes record, state of the patient quality of life (SIBDQ)
T1 3 months
Clinical evaluation of the disease status with Mayo Partial Score, Bristol Stool Chart, pain VAS scale, inflammatory indexes record, state of the patient quality of life (SIBDQ)
T2 6 months
Clinical evaluation of the disease status with Mayo Partial Score, Bristol Stool Chart, pain VAS scale, inflammatory indexes record, state of the patient quality of life (SIBDQ)

In FIGS. 4-A, 4-B, 4-C, 4-D, the most important results at T1=3 months and at T2=6 months are reported.

In FIG. 4-A the group A assuming 2 tablets according to the present invention is improving (reduction vs T0 an vs T1) the inflammatory profile with respect to the control group, wherein an initial rise of the faecal calprotectin can be noted.

As follows from FIG. 4-B even the quality of life of Group A improves (increases) within a treatment time lapse of three and six months. By contrast Group C does not report any improvement in the quality of life.

In FIG. 4C it follows that the general status of the disease, clinically observed by the mps test, improves (score reduction) within group A such to exclude the patient from the active-RCU criteria (MPS test between 2 and 7), unlike the control group from which it follows that values higher than 2 show a still active RCU.

In FIG. 4D it follows that the abdominal pain perception (VAS scale 0-10), clinically observed by means of the VAS test, improves (score reduction) in group A unlike the control group from which a worsening of the symptom is clear.

REFERENCES 1. http://www.treccani.it/encyclopedia/inflammazione/
2. Marina Risi. Il regolatore dell'inflammazione. PNEI News. 2012; 6
3. Danese, S. and C. Fiocchi, Etiopathogenesis of inflammatory bowel diseases. World J Gastroenterol, 2006. 12 (30): p. 4807-12.
4. Danese, S., Immune and nonimmune components orchestrate the pathogenesis of inflammatory bowel disease. Am J Physiol Gastrointest Liver Physiol, 2011. 300(5): p. G716-22.
5. Danese, S., New therapies for inflammatory bowel disease: from the bench to the bedside. Gut, 2012. 61(6): p. 918-32.
6. Fiorino, G., et al., Leukocyte traffic control: a novel therapeutic strategy for inflammatory bowel disease. Expert Rev Clin Immunol, 2010. 6(4): p. 567-72
7. Camacho-Barquero, L., et al., Curcumin, a *Curcuma longa* constituent, acts on MAPK p38 pathway modulating COX-2 and iNOS expression in chronic experimental colitis. Int Immunopharmacol, 2007. 7(3): p. 333-42.
8. Deguchi, Y., et al., Curcumin prevents the development of dextran sulfate Sodium (DSS)-induced experimental colitis. Dig Dis Sci, 2007. 52(11): p. 2993-8.
9. Ukil, A., et al., Curcumin, the major component of food flavour turmeric, reduces mucosal injury in trinitrobenzene sulphonic acid-induced colitis. Br J Pharmacol, 2003. 139(2): p. 209-18.
10. Zhang, M., et al., Curcumin regulated shift from Th1 to Th2 in trinitrobenzene sulphonic acid-induced chronic colitis. Acta Pharmacol Sin, 2006. 27(8): p. 1071-7
11. Goel, A., A. B. Kunnumakkara, and B. B. Aggarwal, Curcumin as "Curcumin": from kitchen to clinic. Biochem Pharmacol, 2008. 75(4): p. 787-809.
12. Mun S H et al. Synergistic antibacterial effect of curcumin against methicillin-resistant *Staphylococcus aureus*. Phytomedicine. 2013 Jun. 15; 20(8-9):714-8.
13. Dominik Bettenworth et al. Crohn's disease complicated by intestinal infection with methicillin-resistant *Staphylococcus aureus*. World J Gastroenterol 2013 Jul. 21; 19(27)
14. Kiela, P. R., et al., Effects of *Boswellia serrata* in mouse models of chemically induced colitis. Am J Physiol Gastrointest Liver Physiol, 2005. 288(4): p. G798-808.
15. Krieglstein, C. F., et al., Acetyl-11-keto-beta-boswellic acid, a constituent of a herbal medicine from *Boswellia serrata* resin, attenuates experimental ileitis. Int J Colorectal Dis, 2001. 16(2): p. 88-95.
16. Alsaba F Raja et al. Antistaphylococcal and biofilm inhibitory activities of acetyl-11-keto-b-boswellic acid from *Boswellia serrata*. BMC Microbiology 2011, 11:54
17. Bialonska D et al. The influence of pomegranate by-product and punicalagins on selected groups of human intestinal microbiota. Int J Food Microbiol. 2010

The invention claimed is:

1. A colonic release oral tablet comprising as active ingredients a mixture of dry extracts of turmeric, pomegranate and *Boswellia*, said active ingredients being dispersed in a matrix together with a combination of sodium alginate and hydroxypropylmethylcellulose wherein said colonic release is guaranteed by said combination of sodium alginate and hydroxypropyl methylcellulose being present in the matrix in which the active ingredients are dispersed, in weight ratios comprised between 1:25 and 1:10.

2. The oral tablet according to claim 1, containing a dry extract of black pepper.

3. The oral tablet according to claim 2, wherein the black pepper derives from the fruits of the *Piper nigrum* L. plant, with a minimum titer in piperine of 80%.

4. The oral tablet according to claim 2, containing black pepper in amounts comprised between 1 and 5 mg by weight on the total weight of the tablet.

5. The oral tablet according to claim 1, wherein the dry turmeric extract derives from the *Curcuma longa* L rhizome and has a minimum titer in curcumin and curcuminoids of 90%, the dry pomegranate extract derives from the fruit of *Punica granatum* L and has a minimum titer in ellagic acid of 20%, and the dry *boswellia* extract derives from the *Boswellia serrata* Roxb gum resin and has a minimum titer in boswellic acids of 30%.

6. The oral tablet according to claim 1, wherein the turmeric is contained in amounts comprised between 80 and 150 mg by weight on the total weight of the tablet, the *boswellia* is contained in amounts comprised between 150 and 300 mg, the dry pomegranate extract is contained in amounts between 200 and 350 mg, by weight on the total weight of the tablet.

7. The oral tablet according to claim 1 comprising probiotics.

8. The oral tablet according to claim 1, comprising post-biotics selected from indole and short chain fatty acids, said fatty acids (SCFA) selected from propionic acid, butyric acid and formic acid.

9. The oral tablet according to claim 1, comprising a gastroresistant coating comprising or consisting of shellac.

10. The oral tablet according to claim 1 in the form of a food supplement.

11. A method of treating colonic disorders caused by suspected or confirmed alteration of inflammatory situation and destabilization of microbiota, said method comprising administering to a subject in need thereof the oral tablet according to claim 1 as a coadjuvant.

12. The method according to claim 11, wherein said tablet is administered twice a day.

13. The method according to claim 11, wherein said colonic disorders caused by suspected or confirmed alteration of the inflammatory situation and destabilization of the microbiota are selected from colitis selected from indeterminate, collagen, from drugs and non-specific, diverticular diseases selected among symptomatic uncomplicated diverticulosis or SUDD, diverticulitis, segmental colitis associated with diverticulosis SCAD, inflammatory bowel diseases selected from Ulcerative rectocolitis RCU, Crohn's disease.

* * * * *